MethodsForProducingAlcohol

US008753838B2

(12) United States Patent
Um et al.

(10) Patent No.: US 8,753,838 B2
(45) Date of Patent: Jun. 17, 2014

(54) METHOD FOR PRODUCING ALCOHOL USING BIOETHANOL WASTE FERMENTED SOLUTION

(75) Inventors: Youngsoon Um, Seoul (KR); Byoung-In Sang, Seoul (KR); Jae Hyung Ahn, Seoul (KR)

(73) Assignee: Korea Institute of Science and Technology (KR)

( * ) Notice: Subject to any disclaimer, the term of this patent is extended or adjusted under 35 U.S.C. 154(b) by 230 days.

(21) Appl. No.: 13/034,338

(22) Filed: Feb. 24, 2011

(65) Prior Publication Data

US 2011/0207191 A1    Aug. 25, 2011

(30) Foreign Application Priority Data

Feb. 25, 2010    (KR) ........................ 10-2010-0017274

(51) Int. Cl.
*C12P 1/00* (2006.01)
*C12P 7/04* (2006.01)
*C12P 7/16* (2006.01)
*C12P 7/06* (2006.01)
*C12P 7/08* (2006.01)

(52) U.S. Cl.
USPC ............. 435/41; 435/157; 435/160; 435/161; 435/163

(58) Field of Classification Search
None
See application file for complete search history.

(56) References Cited

U.S. PATENT DOCUMENTS

| 6,953,684 B2 * | 10/2005 | Dunn-Coleman et al. . 435/252.3 |
| 2006/0177916 A1 * | 8/2006 | Stewart et al. ................ 435/161 |
| 2008/0311640 A1 * | 12/2008 | Cox et al. ...................... 435/168 |

FOREIGN PATENT DOCUMENTS

| KR | 1020070077476 | 7/2007 |
| KR | 100863158 | 10/2008 |
| KR | 1020110049347 | 5/2011 |

OTHER PUBLICATIONS

Taconi et al. Environmental Progress & Sustainable Energy, vol. 28, Issue 1, Article first published online: Mar. 10, 2009.*
Temudo et al. Biotechnology and Bioengineering vol. 100, Issue 6, Article first published online: Feb. 29, 2008.*
Aldiguier et al. Bioprocess Biosyst Eng (2004) 26: 217-222.*
da Silva et al. Biotechnology Advances 27 (2009) 30-39.*
Sakai et al. Biotechnology and Bioengineering, vol. 98, Issue 2, Article first published online: Mar. 27, 2007.*
Simonetti et al. Green Chem., 2007, 9, 1073-1083.*
Wang et al. Biotechnology Advances 19 (2001) 201-223.*
Scanes et al. S. Afr. J. Enol. Vitic, vol. 19, No. 1,1998.*
Dabrock et al.; "Parameters Affecting Solvent Production by *Clostridium pasteurianum*" Applied and Environmental Microbiology, vol. 58, No. 4, Apr. 1992, pp. 1233-1239.
Korean Office Action for Application No. 10-2010-0017274 issued Aug. 19, 2011 with English translation.
Ahn et al., "Butanol production from thin stillage using *Clostridium pasteurianum*", Bioresource Technology, 102, 2011, pp. 4934-4937.
Kim et al., "Composition of corn dry-grind ethanol by-products: DDGS, wet cake, and thin stillage", Bioresource Technology, 99, 2008, pp. 5165-5176.
Moon et al., "Effect of Biodiesel-derived Raw Glycerol on 1,3-Propanediol Production by Different Microorganisms", Appl Biochem Biotechnol, 161, 2010, pp. 502-510.
Venkataramanan et al., "Impact of impurities in biodiesel-derived crude glycerol on the fermentation by *Clostridium pasteurianum* ATCC 6013", Appl Microbiol Biotechnol, 93, 2012, pp. 1325-1335.

* cited by examiner

*Primary Examiner* — Chris R Tate
*Assistant Examiner* — Douglas F White
(74) *Attorney, Agent, or Firm* — Cantor Colburn LLP

(57) ABSTRACT

Provided is a method for producing alcohol or hydrogen gas comprising culturing alcohol-producing microorganisms in a waste fermented solution generated from the bioethanol production process. Glycerol included in the waste fermented solution generated from the bioethanol production process is converted by the microorganisms to butanol under an anaerobic condition. Since the waste fermented solution generated from the bioethanol production process can be utilized as a source of a biofuel, environmental and energy problems can be solved at once.

20 Claims, 13 Drawing Sheets

METHOD FOR PRODUCING ALCOHOL USING BIOETHANOL WASTE FERMENTED SOLUTION

CROSS-REFERENCE TO RELATED APPLICATION

This application claims priority to Korean Patent Application No. 10-2010-0017274, filed on Feb. 25, 2010, and all the benefits accruing therefrom under 35 U.S.C. §119, the contents of which in its entirety are herein incorporated by reference.

BACKGROUND

1. Field

The present disclosure relates to preparation of alcohol by culturing alcohol-producing microorganisms in a waste fermented solution remaining after distilling ethanol in the process of producing bioethanol.

2. Description of the Related Art

Due to high oil prices and concerns on global warming resulting from the use of fossil fuel, biofuel production is increasing rapidly globally. Especially, the production of bioethanol, which is commercially available by fermentation, has increased steeply. In the US, Brazil, Canada and Sweden, bioethanol is used as automobile fuel. Also, China, Australia and Japan are actively introducing and expanding the use of bioethanol. As for Korea, researches and developments have been made on bioethanol since 1988 with the enactment of the "Alternative Energy Development Promotion Act". The conclusion is that bioethanol may be safely mixed with gasoline in an amount of 3-5%.

Since waste fermented solution is generated in an amount as much as 20 times the produced ethanol from the bioethanol-producing plants, an effective treatment thereof is required. Usually, the waste fermented solution is processed as follows. It is concentrated after centrifugation, or mixed with solid materials and then dried to make animal feed. Some of the waste fermented solution is used to dilute the source material, and the remainder is treated by methane fermentation. There has been no attempt to produce butanol using the waste fermented solution as yet.

Glycerol is one of the fermentation products by yeast. 3-5.3 g of glycerol is produced from 100 g of glucose. Since the ethanol waste fermented solution contains glycerol as well as many other byproducts such as lactic acid, acetic acid, ethanol, etc., an effective treatment of the waste fermented solution using them will be necessary.

SUMMARY

The present disclosure is directed to providing a method for producing alcohol using a waste fermented solution in order to effectively treat the waste fermented solution generated in an amount as much as 20 times that of bioethanol, there by solving the environmental and energy problems at the same time.

In one aspect, there is provided a method for producing alcohol including culturing alcohol-producing microorganisms in a waste fermented solution produced during the bioethanol production process.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1:
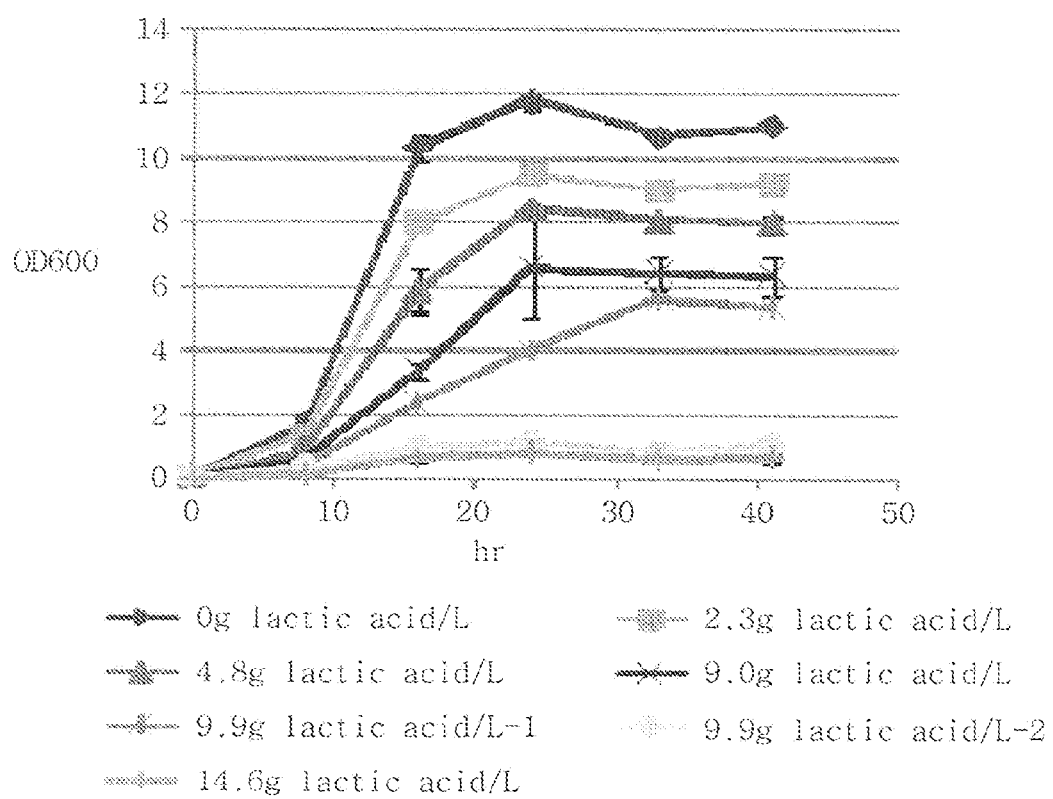
FIG. 1 shows cell growth after inoculation of *Clostridium pasteurianum* to a medium containing lactic acid.

Exemplary embodiments now will be described more fully hereinafter with reference to the accompanying drawings, in which exemplary embodiments are shown. The present disclosure may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art. In the description, details of well-known features and techniques may be omitted to avoid unnecessarily obscuring the presented embodiments.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The present disclosure provides a method for producing alcohol comprising culturing alcohol-producing microorganisms in a waste fermented solution produced during the bioethanol production process.

In an embodiment of the present disclosure, wherein alcohol may be one selected from a group consisting of butanol, 1,3-propanediol and ethanol.

In an embodiment of the present disclosure, the alcohol-producing microorganism is not particularly limited, but it may be a alcohol-producing microorganism belonging to the genus *Clostridium* or one obtained from genetic modification. Specifically, it may be *Clostridium pasteurianum*.

In an embodiment of the present disclosure, the method for producing butanol may comprise preparing the waste fermented solution medium prior to the culturing. The preparation of the waste fermented solution medium may comprise: fermenting biomass in a medium containing yeast; and distilling the fermented solution and obtaining the resulting distillate.

The biomass is one containing organic matter as a carbon source for the microorganism. Although not limited thereto, it may be one selected from a group consisting of sugar biomass, lignocellulose biomass, seaweed biomass, and organic waste. The sugar biomass may be one selected from a group consisting of corn, sugarcane, wheat, brown rice and tapioca; the lignocellulose biomass may be one selected from a group consisting of wood, cornstalk, rice straw, and switchgrass; the organic waste may be one selected from food waste, paper waste, wood waste, etc.

The distillate is one remaining after distilling the fermented solution, without removing the yeast.

In an embodiment of the present disclosure, the preparation of the waste fermented solution medium may further comprise adding the distillate to the medium for the fermentation and circulating again at least once and then obtaining the resulting distillate.

In an embodiment of the present disclosure, the preparation of the waste fermented solution medium may further comprise centrifuging or filtering the distillate to obtain a filtrate with the yeast removed. As the distillate is centrifuged or filtered, it is separated into a sludge and a filtrate. The filtrate has the yeast removed.

The ethanol waste fermented solution distillate or filtrate may be used as a alcohol-producing medium without any pretreatment.

In an embodiment of the present disclosure, the preparation of the waste fermented solution medium may further comprise adding the distillate to the medium for the fermentation and circulating again at least once and then obtaining the resulting filtrate.

In an embodiment of the present disclosure, the preparation of the waste fermented solution medium may further comprise adding the filtrate again to the medium for the fermentation and circulating again at least once and then obtaining the resulting distillate or filtrate.

In an embodiment of the present disclosure, a waste fermented solution medium comprising glycerol may be used in the culturing.

The glycerol concentration of the waste fermented solution may be 3 to 60 g/L, specifically 3 to 40 g/L, more specifically 10 to 40 g/L. When the glycerol concentration is greater than 40 g/L, the growth rate of the microorganism may decrease and the alcohol production and glycerol consumption may not increase further. And, when it is less than 3 g/L, alcohol may not be produced sufficiently. The glycerol concentration of the waste fermented solution may be increased, for example, by adding the filtrate or filtrate obtained when preparing the waste fermented solution medium again to the medium for the fermentation and circulating again at least once and then obtaining the resulting distillate or filtrate. Also, glycerol concentration may be increased by electrodialysis, precipitation, etc. of the waste fermented solution distillate or filtrate, and thus obtained glycerol solution may be used as an alcohol-producing medium.

In an embodiment of the present disclosure, a waste fermented solution medium with a pH 5-7 may be used in the cultivation.

In an embodiment of the present disclosure, the pH of the waste fermented solution medium is adjusted using an alkaline agent in the cultivation. Although not being limited thereto, the alkaline agent may be selected from a group consisting of sodium hydroxide (NaOH), potassium hydroxide (KOH), calcium hydroxide ($Ca(OH)_2$) and ammonia water ($NH_4OH$). Specifically, it may be calcium hydroxide or potassium hydroxide. Usually, an ethanol waste fermented solution has a pH of 3-5, which may be adjusted to 5-7 using the alkaline agent.

In an embodiment of the present disclosure, a waste fermented solution medium comprising at least one organic matter selected from a group consisting of hexose, pentose, disaccharide, polysaccharide, hydrolyzed protein and combination thereof may be used in the culturing. The organic matters are remained after ethanol-distillation followed by bioethanol fermentation.

In an embodiment of the present disclosure, a waste fermented solution medium comprising lactic acid may be used in the culturing.

The lactic acid concentration of the waste fermented solution may be 10 g/L or less. When the lactic acid is comprised in the waste fermented solution at a concentration 10 g/L or less, an improved butanol-producing effect is obtained as compared to when lactic acid is absent (see FIG. 4).

In an embodiment of the present disclosure, a waste fermented solution medium comprising at least one selected from a group consisting of acetic acid, ethanol and combination thereof may be used in said culturing. Specifically, the acetic acid concentration of the waste fermented solution may be 10 g/L or less, and the ethanol concentration of the waste fermented solution may be 10 g/L or less. When the concentration of acetic acid exceeds 10 g/L, the growth of *Clostridium pasteurianum* may be inhibited and the production of butanol may decrease due to the increased production of byproducts such as butyric acid. And, when the concentration of ethanol exceeds 10 g/L, the growth of *Clostridium pasteurianum* may be inhibited.

In an embodiment of the present disclosure, the method for producing alcohol may comprise removing lactic acid for the concentration less than 10 g/L in said culturing. The concentration of lactic acid may be removed by using an ion-exchange resin. Besides, the concentration of lactic acid may be removed by precipitation, extraction, adsorption, reactive distillation, electrodialysis, nanofiltration, or the like.

EXAMPLES

The examples and experiments will now be described. The following examples and experiments are for illustrative purposes only and not intended to limit the scope of the present disclosure.

Example 1

Inhibition Effect of Lactic Acid, Acetic Acid and Ethanol on Butanol Production The butanol-producing bacterium *Clostridium pasteurianum* (DSM 525) was acquired from the DSMZ (Germany). The medium used for experiment was prepared with primarily distilled water (1 L) by adding the following ingredients: glycerol (30 g), $K_2HPO_4$ (0.5 g), $KH_2PO_4$ (0.5 g), $MnSO_4.H_2O$ (0.01 g), $MgSO_4.7H_2O$ (0.2 g), $FeSO_4.7H_2O$ (0.01 g), NaCl (0.01 g), yeast extract (1 g), $(NH_4)_2SO_4$ (2 g), MES (19.52 g), biotin (0.00001 g), thiamine (0.001 g) and p-aminobenzoic acid (0.001 g).

After adding lactic acid ($C_3H_6O_3$, 0-14.6 g/L), acetic acid ($C_2H_4O_2$, 0-10 g/L) or ethanol ($C_2H_6O$, 0-20 g/L) to the medium, the pH was adjusted to 6.5 using potassium hydroxide (KOH) or sodium hydroxide (NaOH). After placing the medium (50 mL) in a 125-mL serum bottle and removing oxygen by blowing in argon gas, the bottle was sealed with a butyl rubber stopper and an aluminum cap. After sterilizing under high pressure and inoculating *Clostridium pasteurianum* cultured for 1-2 days at 5% (v/v), the bacterium was cultured at 37° C. while shaking at 130 rpm.

Figure 2:
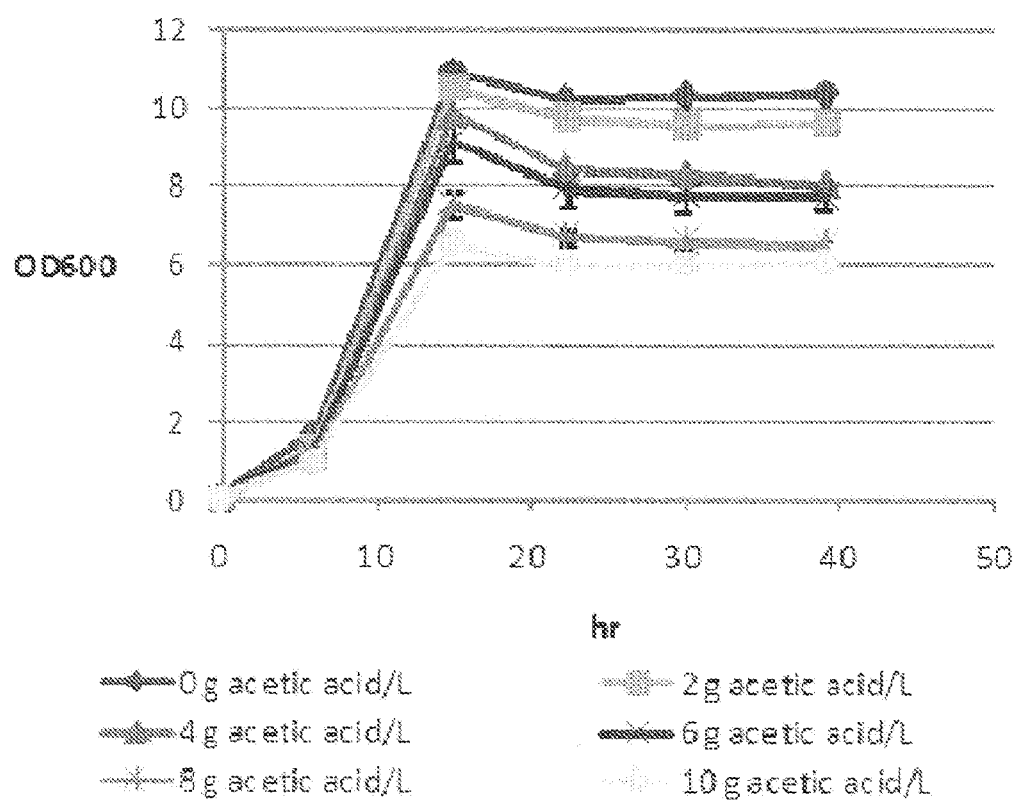
FIG. 2 shows cell growth after inoculation of *Clostridium pasteurianum* to a medium containing acetic acid.
Figure 3:
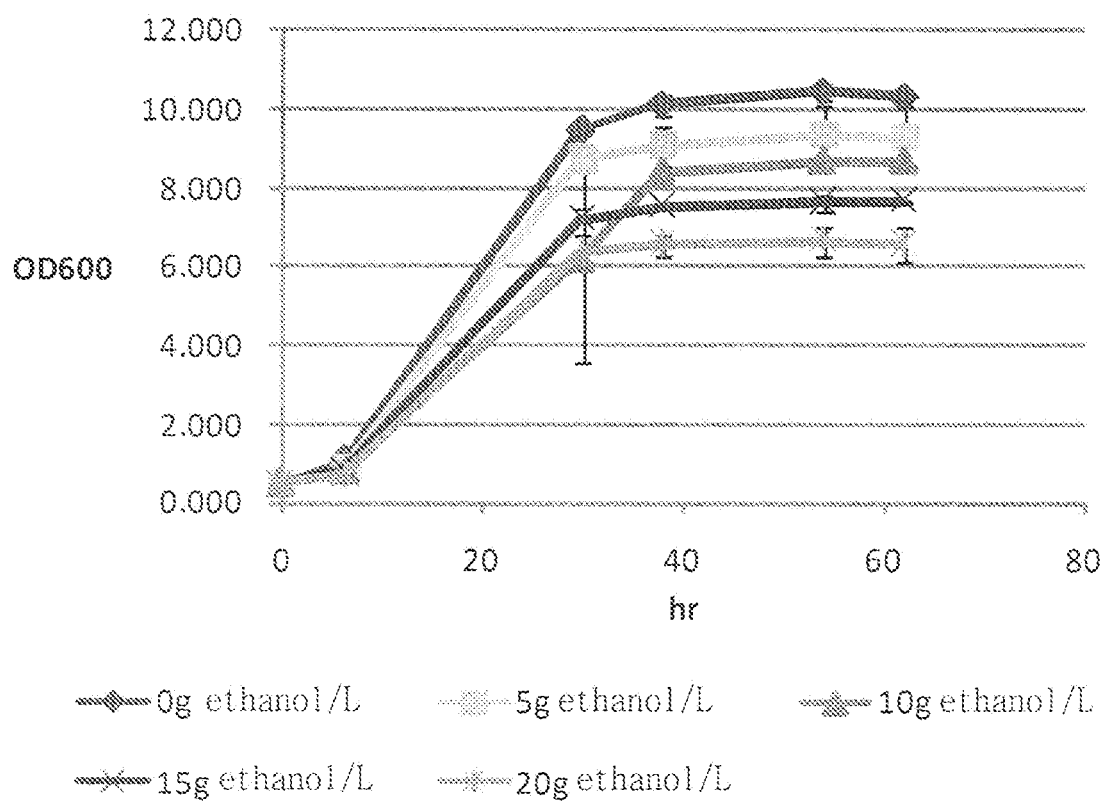
FIG. 3 shows cell growth after inoculation of *Clostridium pasteurianum* to a medium containing ethanol.

Cell growth after inoculation of *Clostridium pasteurianum* to the medium containing lactic acid (FIG. 1), acetic acid (FIG. 2) or ethanol (FIG. 3) is shown in FIGS. 1-3. The cell growth was determined by measuring absorbance (optical density) at 600 nm ($OD_{600}$). Lactic acid, acetic acid and ethanol did not result in severe inhibition of the growth of *Clostridium pasteurianum* up to 10 g/L. 3.5-8 g/L of butanol was produced from 30 g/L of glycerol. The addition of lactic acid resulted in improved production of butanol as compared to when it was not added.

When the lactic acid concentration was 0, 3.9±0.0 g/L of 1,3-propanediol was produced, which amounts to 0.16±0.00 (g/g) of 1,3-propanediol production per glycerol consumption.

Figure 4:
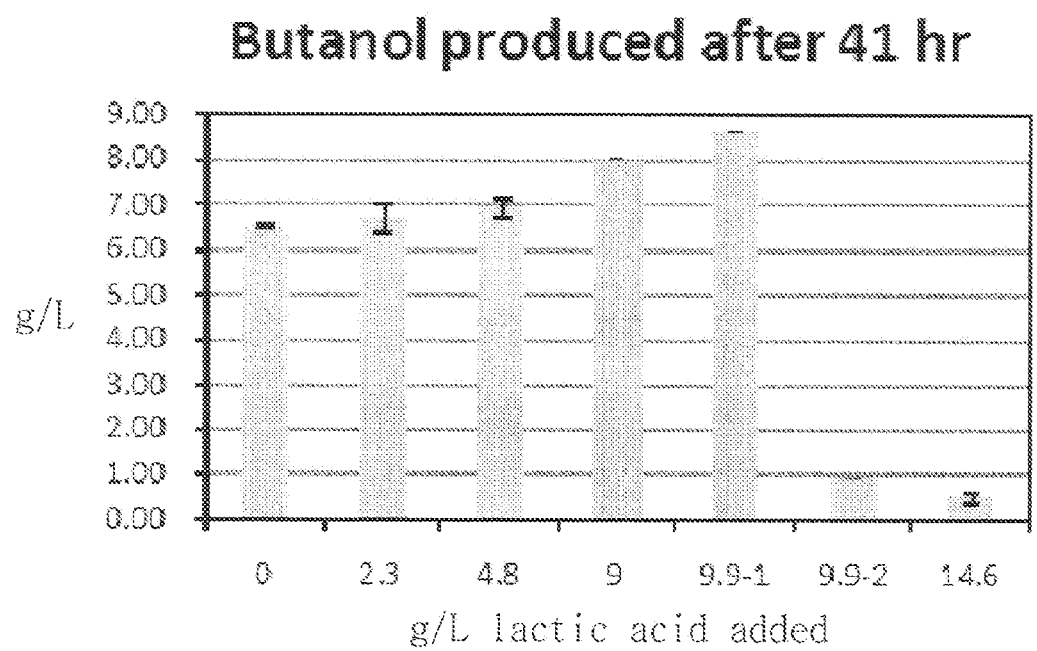
FIG. 4 shows butanol concentration after inoculation of *Clostridium pasteurianum* to a medium containing lactic acid.
Figure 5:
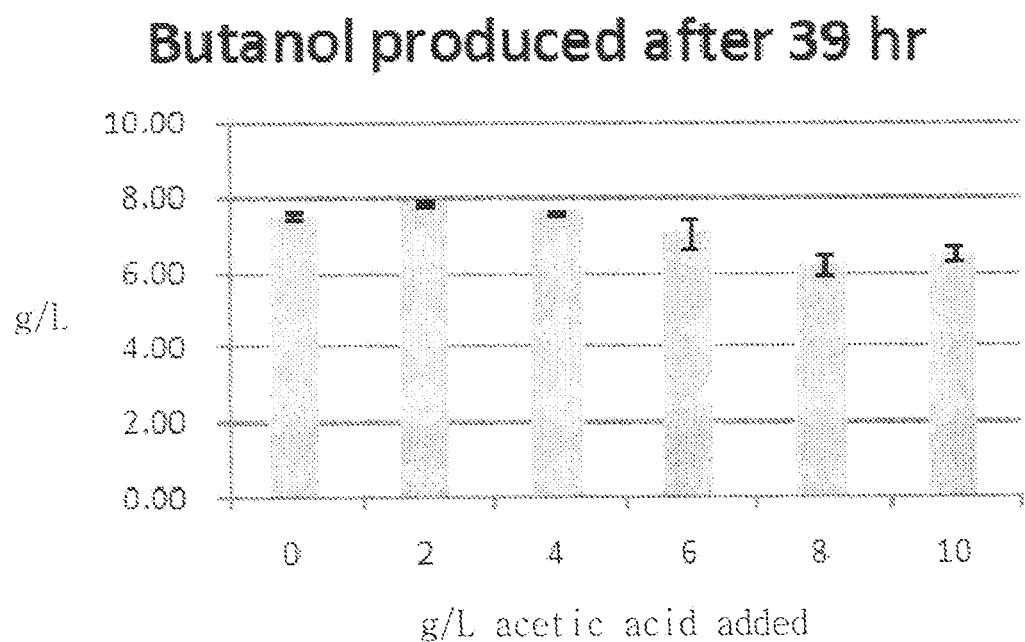
FIG. 5 shows butanol concentration after inoculation of *Clostridium pasteurianum* to a medium containing acetic acid.
Figure 6:
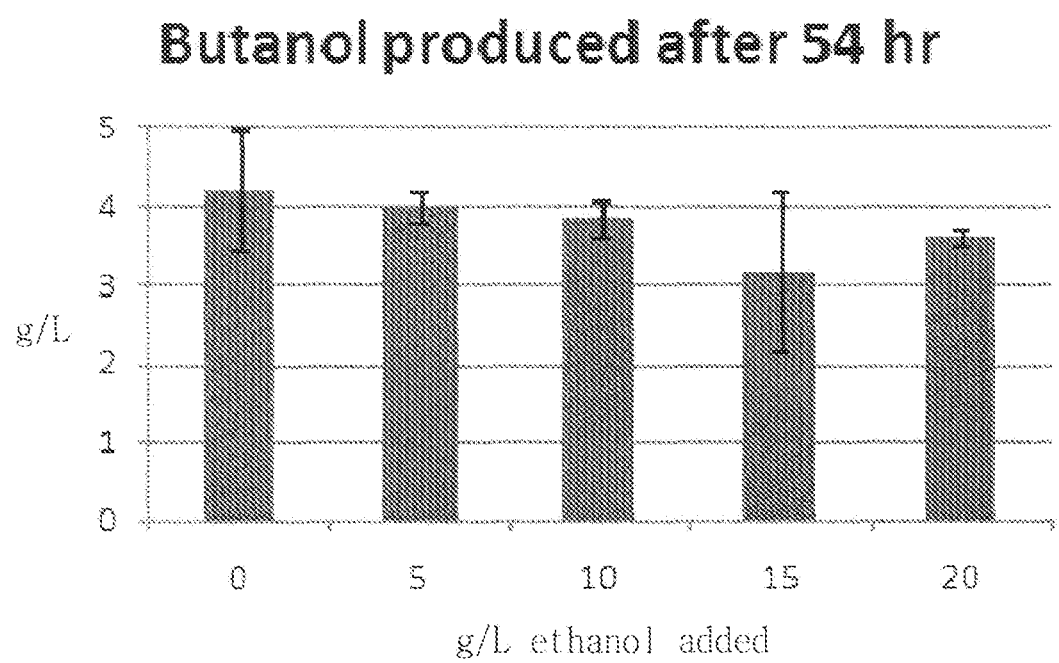
FIG. 6 shows butanol concentration after inoculation of *Clostridium pasteurianum* to a medium containing ethanol.

The butanol concentration after inoculation of *Clostridium pasteurianum* to the medium containing lactic acid (FIG. 4), acetic acid (FIG. 5) or ethanol (FIG. 6) is shown in FIGS. 4-6.

Example 2

Production of Butanol Using Bioethanol Waste Fermented Solution Distillate or Filtrate The ethanol-producing yeast *Saccharomyces cerevisiae* (KCTC 7296) was acquired from the KCTC (Korea). The medium used for ethanol production was prepared with primarily distilled water (1 L) by adding the following ingredients: glucose (220 g), $KH_2PO_4$ (3.0 g), $(NH)_2SO_4$ (7.5 g), $Na_2HPO_4$ (1.19 g), L-glutamic acid (2.18 g), D-/L-lactic acid (5 g), $MgSO_4.7H_2O$ (0.5 g), $ZnSO_4.7H_2O$ (0.04 g), $MnSO_4.4-5H_2O$ (0.0052 g), $CoCl_2.6H_2O$ (0.0005 g), $CuSO_4.5H_2O$ (0.0009 g), $Na_2MoO_4.2H_2O$ (0.00006 g), $CaCl_2.2H_2O$ (0.023 g), $(NH_4)_2Fe(SO_4)_6.6H_2O$ (0.023 g), $H_3BO_3$ (0.003 g), calcium pantothenate (0.0108 g), nicotinic acid (0.0108 g), myo-inositol (0.2688 g), thiamine (0.0108 g), pyridoxine (0.0108 g), p-aminobenzoic acid (0.00022 g) and D-biotin (0.00003 g). pH was adjusted to 5 using potassium hydroxide (KOH).

After placing the medium (250 mL) in a 500-mL Erlenmeyer flask, the flask was sealed by capping. After sterilizing under high pressure and inoculating *Saccharomyces cerevisiae* cultured for 1-2 days at 10% (v/v), the yeast was cultured at 30° C. for 4 days while shaking at 130 rpm. 106.4 g/L of ethanol was produced. Fractional distillation of the medium resulted in a waste fermented solution (distillate) of pH 3.9 containing of ethanol (1.3 g/L), acetic acid (2.5 g/L), 2,3-butanediol (4.1 g/L), glucose (0.13 g/L), lactic acid (3.7 g/L) and glycerol (19.2 g/L).

A portion of the waste fermented solution was filtered through a 0.45-µm filter to obtain a filtrate with the yeast removed. Each of the waste fermented solution distillate and filtrate was prepared into pH 4.9, 5.9 and 6.9 waste fermented solutions using a 5 N potassium hydroxide (KOH) solution. After placing each waste fermented solution (50 mL) in a 125-mL serum bottle and removing oxygen by blowing in argon gas, the bottle was sealed with a butyl rubber stopper and an aluminum cap. After sterilizing under high pressure and inoculating *Clostridium pasteurianum* cultured for 1-2 days at 5% (v/v), the bacterium was cultured at 37° C. while shaking at 130 rpm.

Figure 7:
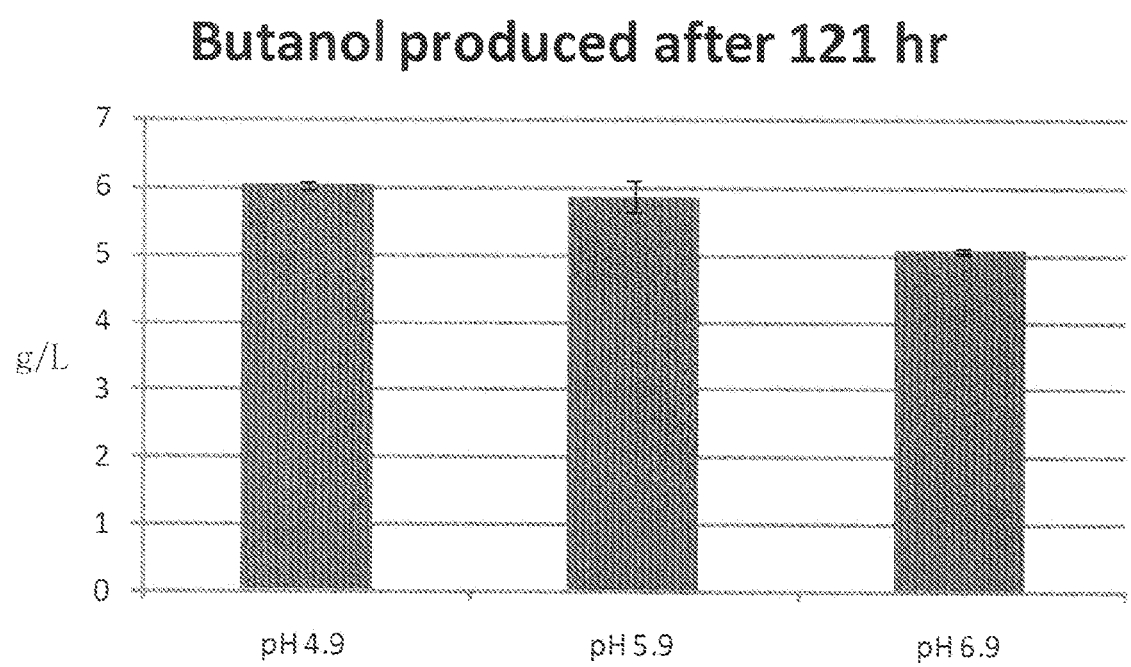
FIG. 7 shows butanol concentration after inoculation of *Clostridium pasteurianum* to an ethanol waste fermented solution distillate in Example 2.
Figure 8:
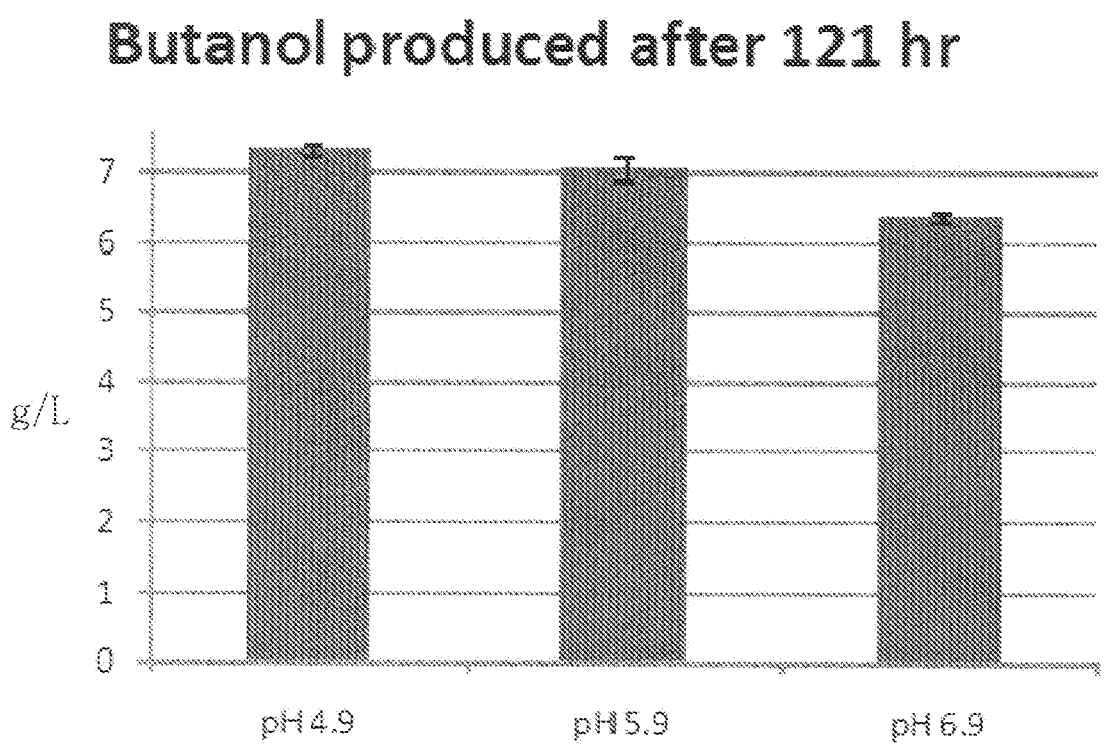
FIG. 8 shows butanol concentration after inoculation of *Clostridium pasteurianum* to an ethanol waste fermented solution filtrate in Example 2.

Cell growth and butanol concentration after inoculation of *Clostridium pasteurianum* to the waste fermented solution distillate (FIG. 7) or filtrate (FIG. 8) are shown in FIGS. 7 and 8.

When pH was not adjusted, i.e. at the initial pH of 3.9, *Clostridium pasteurianum* did not grow at all. When the initial pH was adjusted to 4.9, 5.9 and 6.9, 5-9 g/L of butanol was produced. There was no significant difference in the growth of *Clostridium pasteurianum* between the waste fermented solution distillate and filtrate.

Glycerol consumption and production of butanol, butyric acid and 1,3-propanediol (unit: g/L) from the ethanol waste fermented solution by *Clostridium pasteurianum* depending on initial pH are given in Table 1.

TABLE 1

|  | Ethanol waste fermented solution distillate | | | Ethanol waste fermented solution filtrate (0.45-µm filter) | | |
| --- | --- | --- | --- | --- | --- | --- |
| Initial pH | 4.9 | 5.9 | 6.9 | 4.9 | 5.9 | 6.9 |
| Glycerol consumption | 16.4 ± 4.3 | 18.8 ± 0.3 | 19.6 ± 0.7 | 18.0 ± 0.2 | 17.9 ± 0.4 | 18.9 ± 0.2 |

TABLE 1-continued

| | Ethanol waste fermented solution distillate | | | Ethanol waste fermented solution filtrate (0.45-μm filter) | | |
|---|---|---|---|---|---|---|
| Initial pH | 4.9 | 5.9 | 6.9 | 4.9 | 5.9 | 6.9 |
| Butanol | 6.0 ± 0.1 | 5.9 ± 0.2 | 5.1 ± 0.0 | 7.3 ± 0.1 | 7.1 ± 0.2 | 6.4 ± 0.1 |
| | (0.38 ± 0.10)** | (0.31 ± 0.10)** | (0.26 ± 0.10)** | (0.41 ± 0.00)** | (0.40 ± 0.02)** | (0.34 ± 0.10)** |
| Butyric acid | 0.5 ± 0.1 | 0.6 ± 0.0 | 1.2 ± 0.1 | 0.3 ± 0.0 | 0.6 ± 0.1 | 1.5 ± 0.1 |
| | (0.030 ± 0.004)** | (0.032 ± 0.002)** | (0.061 ± 0.001)** | (0.017 ± 0.002)** | (0.035 ± 0.006)** | (0.081 ± 0.005)** |
| 1,3-Propanediol | 0.0 ± 0.0 | 0.0 ± 0.0 | 0.6 ± 0.0 | 0.0 ± 0.0 | 0.4 ± 0.0 | 0.7 ± 0.1 |
| | (0.000 ± 0.000)** | (0.000 ± 0.000)** | (0.029 ± 0.002)** | (0.000 ± 0.000)** | (0.023 ± 0.001)** | (0.036 ± 0.002)** |

*Measurement was made 121 hours after inoculation of Clostridium pasteurianum (C. pasteurianum) DSM 525.
**Production/glycerol consumption (g/g).

As seen from Table 1, no or less than 1 g/L of 1,3-propanediol was produced when the ethanol waste fermented solution according to the present disclosure was used. The production of 1,3-propanediol per glycerol consumption was 0.000-0.036, less than ¼ of that when the medium of Example 1 was used (0.16). This suggests that the ethanol waste fermented solution is favorable for butanol production since the decreased 1,3-propanediol production means increased glycerol that can be converted to butanol.

Example 3

Effect of Bioethanol Waste Fermented Solution on Cell Growth

In order to confirm the promotion effect of Clostridium pasteurianum growth of the ethanol waste fermented solution, Clostridium pasteurianum was inoculated to a medium that had been or had not been subjected to ethanol fermentation. The medium prior to ethanol fermentation (ethanol-producing medium) was prepared in the same manner as that for culturing of Saccharomyces cerevisiae in Example 2, except for adding glycerol (12-14 g/L) instead of glucose as carbon source and adjusting pH to 5-7 using potassium hydroxide. Since the ethanol-fermented medium (ethanol waste fermented solution) contained 12 g/L of glycerol, it was adjusted to pH 5-7 using potassium hydroxide.

Figure 9:
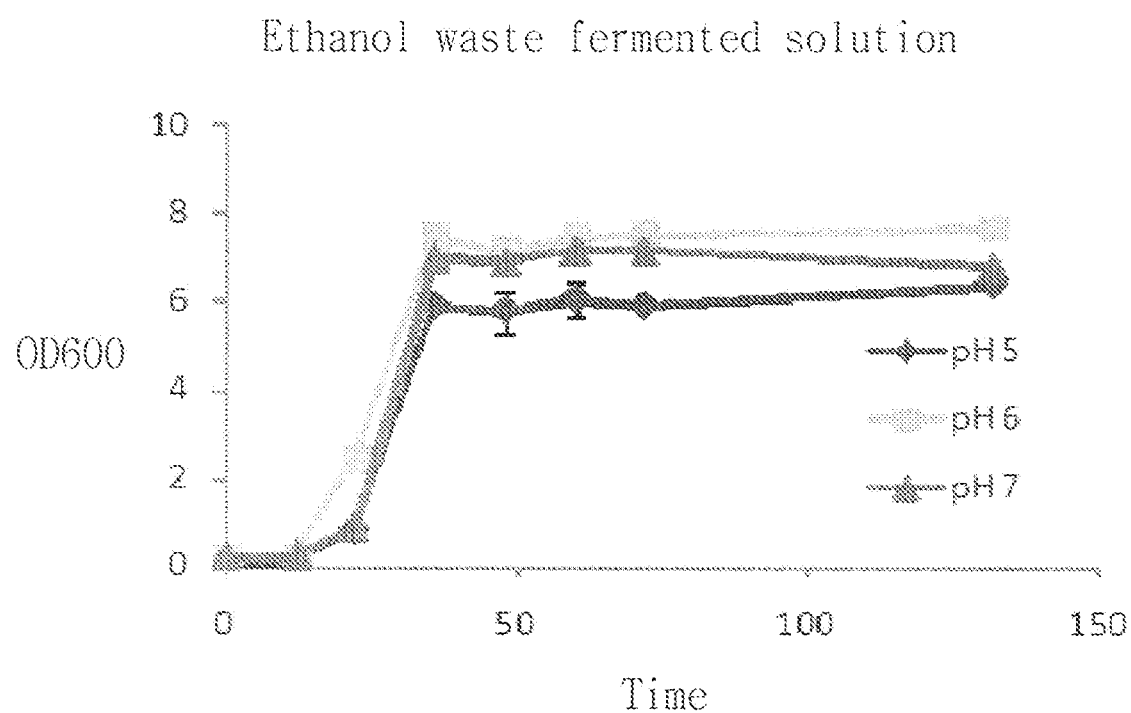
FIG. 9 shows cell growth after inoculation of *Clostridium pasteurianum* to an ethanol waste fermented solution filtrate in Example 3 depending on initial pH.
Figure 10:
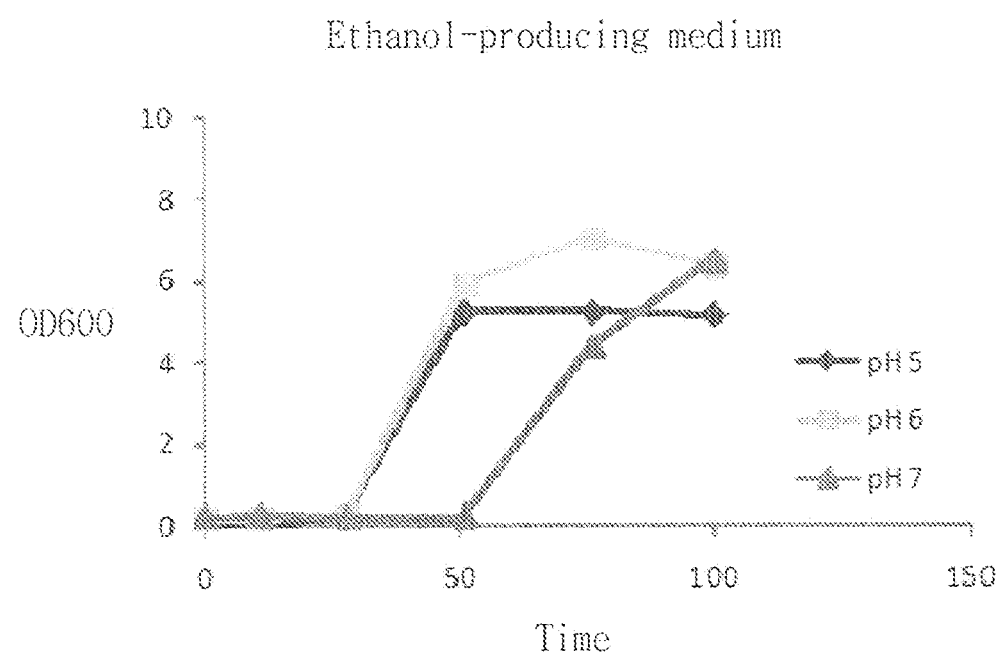
FIG. 10 shows cell growth after inoculation of *Clostridium pasteurianum* to a medium (ethanol-producing medium) before ethanol fermentation in Example 3 depending on initial pH.

Cell growth of Clostridium pasteurianum (C. pasteurianum DSM 525) in the ethanol waste fermented solution is shown in FIG. 9, and that in the medium prior to ethanol fermentation (ethanol-producing medium) is shown in FIG. 10. The concentration of formation products after the fermentation is given in Table 2. Clostridium pasteurianum (C. pasteurianum DSM 525) showed faster growth in the ethanol waste fermented solution than in the ethanol-producing medium. Also, butanol production was faster in the ethanol waste fermented solution.

Example 4

Selection of Alkaline Agent for pH Control of Medium

In the experiment for evaluating the effect of lactic acid, acetic acid and ethanol on the growth of Clostridium pasteurianum (C. pasteurianum DSM 525), sodium hydroxide (NaOH) was used to adjust the pH of the medium. Since the ethanol waste fermented solution has a pH of 4-5, the pH needs to be controlled using an alkaline agent in order to produce butanol using the Clostridium pasteurianum (C. pasteurianum DSM 525). In addition to sodium hydroxide, potassium hydroxide (KOH), calcium hydroxide ($Ca(OH)_2$), ammonia water ($NH_4OH$), etc. are available as the alkaline agent. It was investigated whether the growth of Clostridium pasteurianum (C. pasteurianum DSM 525) is affected by the alkaline agents. For this purpose, after adding lactic acid (10 g/L) to the medium of Example 1, pH was adjusted to 6.5 using each alkaline agent.

Figure 11:
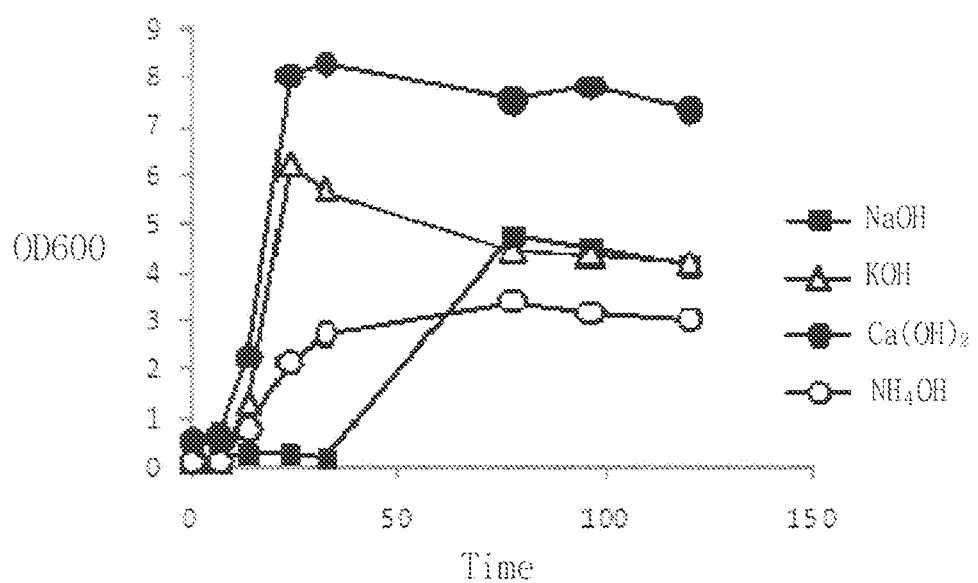
FIG. 11 shows cell growth after inoculation of *Clostridium pasteurianum* to a medium of Example 1 after adding 10 g/L lactic acid and adjusting pH using each alkaline agent.
Figure 12:
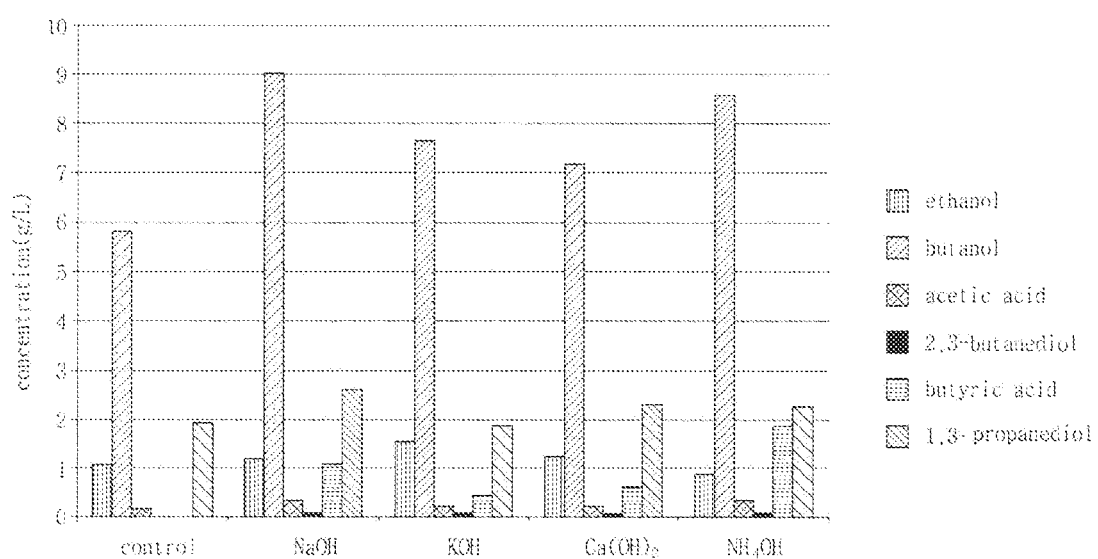
FIG. 12 shows concentration of butanol and other products after inoculation of *Clostridium pasteurianum* to a medium of Example 1 after adding 10 g/L lactic acid and adjusting pH using each alkaline agent.

FIG. 11 shows the growth of Clostridium pasteurianum (C. pasteurianum DSM 525) in the medium after adding 10 g/L lactic acid and adjusting pH using each alkaline agent, and FIG. 12 shows the concentration of butanol and other products. The cell growth was faster in the order of calcium hydroxide, potassium hydroxide, ammonia water and sodium hydroxide, but butanol production was improved by 1-1.5 g/L when sodium hydroxide or ammonia water was used. It was confirmed that sodium inhibits the growth of the microorganism as compared to potassium.

Example 5

Removal of Lactic Acid Using Ion Exchange Resin

Figure 13:
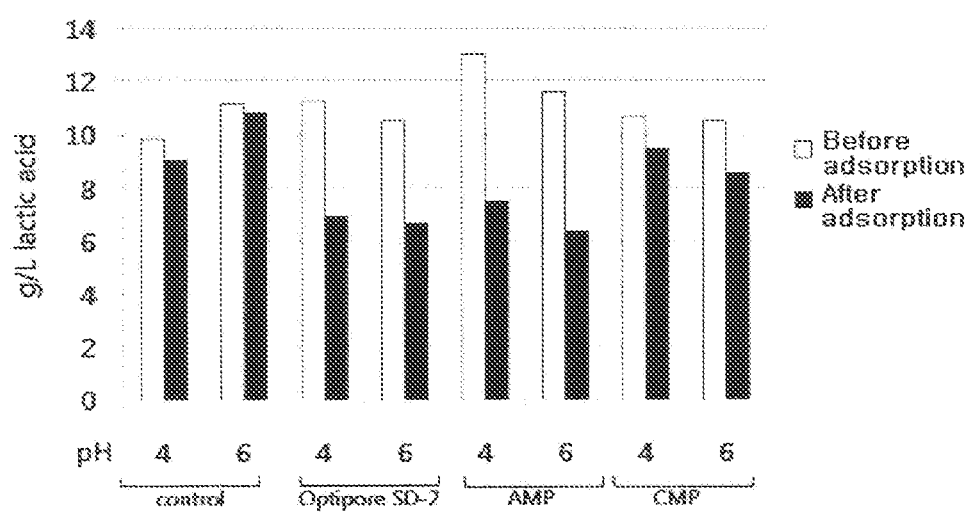
FIG. 13 shows a result of lactic acid removal experiment using an ion exchange resin (The ion exchange resin was Optipore SD-2, AMP or CMP. pH was adjusted to 4 or 6. Change of lactic acid concentration before and after incubation without adding an ion exchange resin was monitored as control.).

FIG. 13 shows the change in lactic acid concentration after adding an ion exchange resin (1 g) to a solution (20 mL)

TABLE 2

| Initial pH | Medium | 5.0 | 6.0 | 7.0 |
|---|---|---|---|---|
| Glycerol consumption | Ethanol waste fermented solution* | 10.5 ± 1.1 | 11.8 ± 0.7 | 11.7 ± 0.2 |
| | Ethanol-producing medium** | 14.0 ± 0.4 | 12.1 ± 0.4 | 12.7 ± 0.4 |
| Butanol | Ethanol waste fermented solution* | 4.0 ± 0.5 | 4.0 ± 0.0 | 3.0 ± 0.2 |
| | Ethanol-producing medium** | 2.3 ± 0.1 | 3.4 ± 0.0 | 2.9 ± 0.1 |
| Butyric acid | Ethanol waste fermented solution* | 0.2 ± 0.0 | 0.5 ± 0.1 | 1.5 ± 0.0 |
| | Ethanol-producing medium** | 0.1 ± 0.0 | 0.3 ± 0.0 | 0.7 ± 0.1 |
| 1,3-Propanediol | Ethanol waste fermented solution* | 0.4 ± 0.1 | 0.6 ± 0.0 | 1.7 ± 0.2 |
| | Ethanol-producing medium** | 0.6 ± 0.0 | 0.8 ± 0.1 | 1.6 ± 0.1 |

*Measurement made after 132 hours
**Measurement made after 100 hours containing glycerol (20 g/L) and lactic acid (10-13 g/L) and stirring at 37° C. When the ion exchange resin was not added, the lactic acid concentration decreased by 3-8% after the incubation. In contrast, when the ion exchange resin was added, the lactic acid concentration decreased by 36-39% (Optipore SD-2), 43-45% (AMP) or 11-19% (CMP). When the pH was adjusted to 4 or 6, no change in the removal efficiency depending on pH was observed. Also, no glycerol adsorption was observed. Thus, when the ethanol waste fermented solution has a high lactic acid concentration, the ion exchange resin Optipore SD-2 or AMP may be used to reduce the lactic acid concentration.

Example 6

Production of Butanol Using Industrial Waste Fermented Solution

Table 3 shows a result of analyzing the ingredients of ethanol waste fermented solutions (unit: g/L).

TABLE 3

| Ingredients | Laboratory produced* | Jinro Distillers |
|---|---|---|
| Ethanol (before distillation) | 102.2 ± 12.9 | Indeterminate |
| Ethanol | 0.6 ± 0.7 | 0.29 |
| pH | 3.7 ± 0.2 | 3.65 |
| Glycerol | 19.0 ± 3.9 | 5.06 |
| Acetic acid | 1.3 ± 0.8 | 1.01 |
| 2,3-Butanediol | 4.6 ± 0.9 | 0.43 |
| Glucose | 0.4 ± 0.4 | Not detected |
| Lactic acid | 5.0 ± 1.2 | 4.8 |

*Mean ± standard deviation of 3 measurements

As seen from Table 3, the laboratory-produced waste fermented solution was similar to that of Jinro in pH, acetic acid, residual ethanol and glucose. 4.8 g/L of lactic acid was detected from the Jinro's waste fermented solution. Glycerol and 2,3-butanediol were about 4 times higher in the laboratory-produced solution.

Table 4 shows glycerol consumption and production of butanol, butyric acid and 1,3-propanediol (unit: g/L) after inoculation of Clostridium pasteurianum (C. pasteurianum DSM 525) to the ethanol waste fermented solution of Jinro Distillers depending on initial pH. Clostridium pasteurianum (C. pasteurianum DSM 525) produced 6.5-7.2 g/L of butanol from the Jinro's waste fermented solution. The butanol production per glycerol consumption increased as the initial pH decreased, as when the laboratory-produced ethanol waste fermented solution was used. However, the production of butyric acid and 1,3-propanediol was more than when the laboratory-produced solution was used. The glycerol consumption showed a different pattern from that when the laboratory-produced solution was used. The butanol production per glycerol consumption was 0.32-0.44.

TABLE 4

| Initial pH | 5.0* | 6.0** | 7.0** |
|---|---|---|---|
| Glycerol consumption | 15.9 ± 0.7 | 18.9 ± 0.9 | 20.2 ± 0.2 |
| Butanol | 6.9 ± 0.0 | 7.2 ± 0.0 | 6.5 ± 0.1 |
|  | (0.44 ± 0.02)*** | (0.38 ± 0.02)*** | (0.34 ± 0.00)*** |
| Butyric acid | 1.7 ± 0.0 | 2.9 ± 0.1 | 2.7 ± 0.0 |
|  | (0.11 ± 0.01)*** | (0.15 ± 0.01)*** | (0.13 ± 0.00)*** |

TABLE 4-continued

| Initial pH | 5.0* | 6.0** | 7.0** |
|---|---|---|---|
| 1,3-Propanediol | 2.7 ± 0.1 | 2.5 ± 0.0 | 2.5 ± 0.2 |
|  | (0.17 ± 0.01)*** | (0.13 ± 0.01)*** | (0.12 ± 0.01)*** |

*Measurement made after 72 hours
**Measurement made after 48 hours
***Production/glycerol consumption (g/g)

The present disclosure provides a method for producing butanol from the waste generated during the bioethanol production process, which can be used as a biofuel. Thus, the low economical efficiency problem of the bioethanol production process can be resolved and the effect on the environment can be reduced by lowering the high concentration of organic matter of the waste fermented solution.

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A method for producing alcohol or hydrogen gas comprising
    adding alcohol-producing microorganisms to a waste fermented solution medium produced during a bioethanol production process for a suitable time and under suitable conditions to produce said alcohol or hydrogen gas,
    wherein the waste fermented solution medium comprises 3 to 40 g/L glycerol and lactic acid, wherein the concentration of lactic acid is greater than 0 g/L and no more than 10 g/L.

2. The method for producing alcohol or hydrogen gas according to claim 1, wherein the alcohol is one selected from the group consisting of butanol, 1,3-propanediol and ethanol.

3. The method for producing alcohol or hydrogen gas according to claim 1, wherein the alcohol-producing microorganism belongs to the genus Clostridium.

4. The method for producing alcohol or hydrogen gas according to claim 1, wherein the alcohol-producing microorganism is Clostridium pasteurianum.

5. The method for producing alcohol or hydrogen gas according to claim 1, wherein the alcohol-producing microorganism is an alcohol-producing microorganism obtained from genetic modification.

6. The method for producing alcohol or hydrogen gas according to claim 1, which comprises
    preparing the waste fermented solution medium prior to said adding, and said preparing the waste fermented solution medium comprises:
    fermenting biomass in a medium containing yeast; and
    distilling the fermented solution and obtaining the resulting distillate.

7. The method for producing alcohol or hydrogen gas according to claim 6, wherein said preparing the waste fermented solution medium further comprises
    adding the distillate to the medium for said fermenting and circulating again at least once and then obtaining the resulting distillate.

8. The method for producing alcohol or hydrogen gas according to claim 6, wherein said preparing the waste fermented solution medium further comprises centrifuging or filtering the distillate to obtain a filtrate with the yeast removed.

9. The method for producing alcohol or hydrogen gas according to claim 8, wherein said preparing the waste fermented solution medium further comprises adding the filtrate again to the medium for said fermenting and circulating again at least once and then obtaining the resulting distillate or filtrate.

10. The method for producing alcohol or hydrogen gas according to claim 1, wherein the pH of the waste fermented solution medium is adjusted using an alkaline agent in said adding.

11. The method for producing alcohol or hydrogen gas according to claim 10, wherein the alkaline agent is selected from a group consisting of sodium hydroxide, potassium hydroxide, calcium hydroxide and ammonia water.

12. The method for producing alcohol or hydrogen gas according to claim 1, wherein the waste fermented solution medium comprises at least one organic matters selected from a group consisting of hexose, pentose, disaccharide, polysaccharide, hydrolyzed protein and combination thereof.

13. The method for producing alcohol or hydrogen gas according to claim 1, wherein the waste fermented solution medium comprises at least one selected from a group consisting of acetic acid, ethanol and combination thereof.

14. The method for producing alcohol or hydrogen gas according to claim 13, wherein a concentration of acetic acid is 10 g/L or less.

15. The method for producing alcohol or hydrogen gas according to claim 13, wherein a concentration of ethanol is 10 g/L or less.

16. The method for producing alcohol or hydrogen gas according to claim 1, which comprises controlling concentration of lactic acid to be less than 10 g/L in said adding.

17. The method for producing alcohol or hydrogen gas according to claim 6, wherein the biomass is selected from a group consisting of sugar biomass, lignocellulose biomass, seaweed biomass, and organic waste.

18. The method of claim 1, further comprising culturing the added alcohol-producing microorganisms in the waste fermented solution medium to produce the alcohol.

19. The method of claim 10, wherein the alcohol is butanol, the pH of the wasted feremented solution medium is adjusted to pH 5-7, and the microorganism is *Clostridium pasteurianum*.

20. The method of claim 1, wherein the concentration of glycerol is 10 to 40 g/L.

* * * * *